United States Patent [19]
Beres et al.

[11] Patent Number: 5,312,629
[45] Date of Patent: May 17, 1994

[54] PHARMACEUTICAL COMPOSITION SUITABLE FOR INFLUENCING THE RETICULOENDOTHELIC SYSTEM AND FOR TREATING MUCOVISCIDOSIS AND CHRONIC PAIN SYNDROMES DERIVING FROM DEGENERATIVE LOCOMOTOR DISEASES OR ACCOMPANYING DISEASES OF TUMOROUS ORIGIN, A PROCESS FOR PREPARING SAME

[75] Inventors: József Béres, Kisvárda; József Béres, Jr., Budapest, both of Hungary

[73] Assignee: Béres, Export-Import Rt., Budapest, Hungary

[21] Appl. No.: 736,314

[22] Filed: Jul. 26, 1991

[30] Foreign Application Priority Data

Jul. 24, 1991 [HU] Hungary .................. 2492/91

[51] Int. Cl.$^5$ ............. A61K 33/34; A61K 33/32; A61K 33/26; A61K 33/22
[52] U.S. Cl. ................. 424/638; 424/639; 424/643; 424/646; 424/657; 424/673; 424/682
[58] Field of Search .......... 424/10, 617, 639, 646, 424/643, 638, 657, 673, 682; 514/454

[56] References Cited

FOREIGN PATENT DOCUMENTS 554348  1/1980  Japan.
2022998B 12/1979 United Kingdom.

*Primary Examiner*—Frederick E. Waddell
*Assistant Examiner*—Raymond J. Henley III
*Attorney, Agent, or Firm*—Herbert Dubno; Jonathan Myers

[57] ABSTRACT

The pharmaceutical composition according to the invention consists essentially of:

i) one or more, pharmaceutically acceptable, water soluble compounds of boron, fluorine, magnesium, vanadium, manganese, iron, cobalt, nickel, copper, zinc and molybdenum, which compounds do not precipitate with each other or with the other components of the composition and exhibit a neutral or acidic pH in an aqueous medium;
ii) glycine;
iii) glycerol;
iv) L-(+)-ascorbic acid;
v) succinic acid;
vi) a neutral or acidic and water-soluble, pharmaceutically acceptable salt of ethylenediamine tetraacetic acid;
vii) potassium sodium tartrate; and
viii) L-(+)-tartaric acid. The composition can be used for the treatment of mucoviscidosis and chronic pain syndromes deriving from locomotor diseases or accompanying diseases of tumorous origin.

1 Claim, No Drawings

PHARMACEUTICAL COMPOSITION SUITABLE FOR INFLUENCING THE RETICULOENDOTHELIC SYSTEM AND FOR TREATING MUCOVISCIDOSIS AND CHRONIC PAIN SYNDROMES DERIVING FROM DEGENERATIVE LOCOMOTOR DISEASES OR ACCOMPANYING DISEASES OF TUMOROUS ORIGIN, A PROCESS FOR PREPARING SAME

FIELD OF THE INVENTION

The present invention relates to a pharmaceutical composition suitable for influencing the reticuloendothelic system and for treating mucovisidosis and chronic pain syndromes deriving from degenerative locomotor diseases or accompanying diseases of tumorous origin, and a process for preparing the same.

BACKGROUND OF THE INVENTION

Hungarian patent specification No. 176,202 and British patent specification No. 2,022,998 describe a pharmaceutical composition suitable for influencing the reticuloendothelic system (RES), i.e. the tissue system built up from different tissue types, situated at different anatomical positions or organs of the human or animal organism. The said composition comprises i) a mixture of pharmaceutically acceptable, water-soluble compounds of boron, fluorine, magnesium, vanadium, manganese, iron, cobalt, nickel, copper, zinc and molybdenum, which compounds do not precipitate with each other or with the other components of the composition and have a neutral or acidic pH in an aqueous medium;

ii) glycine;

iii) glycerol;

iv) L-(+)-ascorbic acid;

v) a neutral or acidic, water-soluble salt of a 2'4,5,7-tetrahalofluorescein (according to the present nomenclature: 2',4',5',7'-tetrahalofluorescein);

vi) a neutral or acidic and water-soluble, pharmaceutically acceptable salt of ethylenediaminetetraacetic acid;

vii) potassium sodium tartrate; and the weight ratio of the boron compound : fluorine compound : magnesium compound : vanadium compound : manganese compound : iron compound : cobalt compound : nickel compound : copper compound zinc compound : molybdenum compound : glycine : glycerol: L-(+)-ascorbic acid: 2,4,5,7-tetrahalofluorescein salt: ethylenediaminetetraacetic acid salt: potassium sodium tartrate is 0.01–1:0.02–1:0.4–3:0.02–0.6:0.1–2:1–6:0.1–1:0.02–2:0.05–1:1:0.1–3:0.01–0.8:0.1–2:2–8:0.01–2:0.003–0.5:0.1–3:0.7–10.

The said composition is prepared by dissolving the components in aqueous medium, mixing the same with pharmaceutically acceptable carriers, diluents and/or excipients, then transforming the mixture thus obtained into a pharmaceutical composition in a manner known per se.

According to a preferred embodiment boric acid is used as boron compound; sodium fluoride or vanadium trifluoride is used as fluorine compound; magnesium sulfate or magnesium chloride or the hydrate thereof is used as magnesium compound; ammonium vanadate or vanadium trifluoride is used as vanadium compound; manganese sulfate or manganese chloride or the hydrate thereof is used as manganese compound; iron(II)- or iron(III)-sulfate or the hydrate thereof is used as iron compound; cobalt chloride or cobalt sulfate or the hydrate thereof is used as cobalt compound; nickel chloride or nickel sulfate or the hydrate thereof is used as nickel compound; copper(II)-sulfate or the hydrate thereof is used as copper compound; zinc sulfate or the hydrate thereof is used as zinc compound; ammonium molybdenate or sodium molybdenate is used as molybdenum compound.

According to a further preferred embodiment of the process 2',4',5',7'-tetraiodofluorescein disodium salt is used as tetrahalofluorescein salt, the disodium salt of ethylenediaminetetraacetic acid salt is used as ethylenediaminetetraacetic acid salt and distilled water is used to make up the aqueous medium.

OBJECT OF THE INVENTION

The object of the present invention is to provide a pharmaceutical composition enabling the treatment of mucoviscidosis and chronic pain syndromes accompanying tumorous diseases or deriving from degenerative locomotor disorders, in addition to exhibiting the advantageous properties of the above-mentioned composition.

DESCRIPTION OF THE INVENTION

The invention is based on the recognition that the above object can be achieved if the 2',4',5',7'-tetrahalofluorescein salt is omitted from the above-identified composition, while the composition is supplemented with succinic acid and L-(+)-tartaric acid. The composition thus obtained is suitable for the treatment of the above pain syndroms.

The invention is based on the further recognition that by changing the components of the composition in the above manner, the composition thus obtained potentiates the effect of the conventional pain-killers, such as morphine, used for the treatment of chronic pain syndromes accompanying the tumorous diseases, i.e. the amount and the disadvantageous side-effects of the conventional pain-killers can be reduced, and it the tolerance threshold and the degree of addiction are favorably influenced.

The invention is based on the further recognition that the advantageous properties of the composition described in the above Hungarian and British patent specifications remain practically unchanged if the lower limit of the weight ratio of certain components is reduced.

Thus, the present invention relates to a pharmaceutical composition suitable for influencing the reticuloendothelic system and for the treatment of mucoviscidosis and chronic pain syndromes deriving from degenerative locomotor diseases or accompanying diseases of tumorous origin.

The said pharmaceutical composition comprises i) one or more, pharmaceutically acceptable, water-soluble compounds of boron, fluorine, magnesium, vanadium, manganese, iron, cobalt, nickel, copper, zinc and molybdenum, which compounds do not precipitate with each other or with the other components of the composition and exhibit a neutral or acidic pH in an aqueous medium;

ii) glycine;

iii) glycerol;

iv) L-(+)-ascorbic acid;

v) succinic acid;

vi) a neutral or acidic and water-soluble, pharmaceutically acceptable salt of ethylenediaminetetraacetic acid;

vii) potassium sodium tartrate;

viii) L-(+)-tartaric acid, wherein the mass ratio of the boron compound : fluorine compound : magnesium compound : vanadium compound : manganese compound : iron compound : cobalt compound : nickel compound : copper compound : zinc compound molybdenum compound : glycine : glycerol : L-(+)-ascorbic acid : succinic acid : ethylenediaminetetraacetic acid salt : potassium sodium tartrate : L-(+)-tartaric acid is 0.01–1:0.01–1:0.2–3:0.01–0.6:0.02:–2:0.15–6:0.0-02–1:0.01:2:0.01–1:0.1–3:0.001–0.8:0.1–2:0.2–8:0.-01–2:0.001–2:0.01–3–:0.01–10:00.1–2.

The said composition is prepared by dissolving the above components in aqueous medium, then transforming the mixture thus obtained together with one or more pharmaceutically acceptable diluents and/or excipients into a pharmaceutical composition in a manner known per se.

The pharmaceutical composition according to the invention—similarly to the pharmaceutical composition described in the above-mentioned Hungarian and British patent specifications—is based substantially on water, i.e. the components can be dissolved and mixed in aqueous medium.

In addition to the above-listed components the pharmaceutical composition according to the invention may comprise dissolution-promoting agents, preferably ethanol; buffers suitable for adjusting the desired, pharmaceutically acceptable pH, preferably hydrochloric acid or sulfuric acid; conventional pharmaceutical carriers, diluents and excipients.

If the solvent is distilled water, then the concentration of components i)–viii) may vary within about 0.001 to 10% by weight/volume.

The pharmaceutical composition provided by the invention may be prepared from various complexes which form together a more complicated complex when combined in an aqueous solution while keeping their water-soluble character. The aqueous solution obtained may be concentrated and the concentrate can be absorbed in a suppository mass to produce suppositories or pessaries.

According to a preferred embodiment, the pharmaceutical composition of the invention comprises boric acid as boron compound (preferably in an amount of 0.01 to 1.0% by weight/volume); sodium fluoride or vanadium trifluoride as fluorine compound (preferably in an amount of 0.01 to 1.0% by weight/volume); magnesium sulfate or magnesium chloride or the hydrate thereof as magnesium compound (preferably in an amount of 0.2 to 3.0% by weight/volume); ammonium vanadate or vanadium trifluoride as vanadium compound (preferably in an amount of 0.001 to 0.6% by weight/volume); manganese sulfate hydrate or manganese chloride tetrahydrate as manganese compound (preferably in an amount of 0.02 to 2.0% by weight/volume); iron(II)-sulfate heptahydrate or iron(III)-sulfate as iron compound (preferably in an amount of 0.15 to 6.0% by weight/volume); cobalt chloride hexahydrate or cobalt sulfate heptahydrate as cobalt compound (preferably in an amount of 0.002 to 1.0% by weight/volume); nickel chloride or nickel sulfate heptahydrate as nickel compound (preferably in an amount of 0.01 to 2.0% by weight/volume); copper(II)-sulfate or the pentahydrate thereof as copper compound (preferably in an amount of 0.01 to 1.0% by weight/volume); zinc sulfate or the heptahydrate thereof as zinc compound (preferably in an amount of 0.10 to 3.0% by weight/volume); ammonium molybdenate/(NH$_4$)$_6$Mo$_7$O$_{24}$.4 H$_2$O/or sodium molybdenate (Na$_2$MoO$_4$.2-H$_2$O) as molybdenum compound (preferably in an amount of 0.001 to 0.8% by weight/volume).

The previous and following data relating to concentrations in % by weight/volume units have to be understood in such a way that the amount of the individual components expressed in grams is dissolved in 100 ml solution.

The preferable concentration ranges of the other components of the pharmaceutical composition according to the invention are as follows:

| | |
|---|---|
| glycine | 0.10 to 2.0% by weight/volume |
| glycerol | 0.20 to 8.0% by weight/volume |
| L-(+)-ascorbic acid | 0.01 to 2.0% by weight/volume |
| succinic acid | 0.01 to 2.0% by weight/volume |
| ethylenediaminetetraacetic acid disodium salt | 0.01 to 3.0% by weight/volume |
| potassium sodium tartrate | 0.01 to 10.0% by weight/volume |
| L-(+)-tartaric acid | 0.01 to 2.0% by weight/volume. |

The preferable amount of ethanol (suitably of a concentration of 96% by volume) used as dissolution-promoting agent is 0.05 to 10.0% by weight/volume, while the preferable amount of the pharmaceutically acceptable acid, preferably hydrochloric acid or sulfuric acid, used for adjusting the pH of the solution is 0.05 to 1.0% by weight/volume.

The pH of the pharmaceutical composition of the invention is preferably 1.9 to 4.0. 1 N sulfuric acid or hydrochloric acid is preferably used for adjusting the pH.

The pharmaceutical composition according to the present invention can be administered orally, in the form of drops, or rectally or intravaginally, in the form of suppository or pessary.

A pharmaceutical composition suitable for rectal or vaginal administration is preferably prepared by evaporating the aqueous solution to syrupy consistency and letting it to be absorbed in a suppository mass. The suppositories or pessaries are prepared from this mass in a way conventionally used in the pharmaceutical industry. The suppository mass is preferably prepared from cocoa-butter, carnauba wax or gelatine.

The invention is further illustrated by the following non-limiting examples.

Example 1

100 l of pharmaceutical composition is prepared as follows.

1. Preparation of complexing agents (ligands)

a) 300 g of Selecton B$_2$ (EDTA disodium salt) are dissolved under heating in 4 l of distilled water.

b) 200 g of potassium sodium tartrate are dissolved in 2 l of distilled water.

c) 50 g of succinic acid and 410 g of magnesium sulfate heptahydrate are dissolved under heating in 2 l of distilled water.

d) 50 g of L-(+)-tartaric acid and 94 g of manganese sulfate monohydrate are dissolved in 1 l of distilled water.

e) 60 g of boric acid and 600 g of glycerol (of a concentration of at least 86.4% by weight) are dissolved together in the presence of 200 ml of distilled water under slight heating.

f) 230 g of glycine are dissolved in 800 ml of distilled water under slight heating, then the solution is supplemented with the copper sulfate and then with the zinc sulfate solutions as described under 4.II.

2. 30 g of L-(+)-ascorbic acid are dissolved in 500 ml of distilled water of a temperature of 50° to 60° C. under shaking.

3. In case of necessity, the pH is adjusted to 1.9–4 with L-(+)-ascorbic acid.

4. Preparation of complex groups

Complex I

Into an Erlenmeyer flask of 1 l volume 200 ml of water, 20 g of sodium fluoride and 20 g of ammonium vanadate are charged. After dissolution the solution is poured into a stirring tank of 100 l volume wherein previously 50 l of distilled water have been charged.

Complex II 100 g of copper(II)-sulfate pentahydrate are dissolved in 500 ml of distilled water. In an other flask 500 g of zinc sulfate heptahydrate are dissolved in 1 l of distilled water. First the copper sulfate solution, then the zinc sulfate solution are added to the glycine solution prepared according to 1.f). Thus a bluish-violet solution is obtained which is poured under stirring into the complex I being in the tank.

Complex III

To 1 l of Selecton B$_2$ solution prepared according to 1.a) 10 g of CoCl$_2$.6H$_2$O
35 g of (NH$_4$)$_6$Mo$_7$O$_{24}$.4H$_2$O
52 g of NiSO$_4$.7H$_2$O
8 g of NH$_4$VO$_3$ and 800 ml of distilled water are added and the solid components are dissolved under heating. The solution thus obtained is poured into the solution in the tank.

1000 g of iron(II)-sulfate heptahydrate are separately dissolved in 4 l of distilled water in the presence of 2 l of Selecton B$_2$ solution prepared according to 1.a) and the solution thus obtained is also poured into the tank, then the remaining Selecton B$_2$ solution is also added under stirring. Thus a bluish-green, turbid solution is obtained.

Complex IV 410 g of magnesium sulfate heptahydrate and 50 g of succinic acid are dissolved in 1 l of distilled water under slight heating, then the solution thus obtained is poured under stirring into the solution being in the tank.

Complex V 94 g of manganese sulfate monohydrate and 50 g of L-(+)-tartaric acid are dissolved in 500 ml of distilled water under heating, then the solution thus obtained is poured under stirring into the solution being in the tank.

Complex VI 60 g of boric acid and 600 g of glycerol are dissolved in the presence of 200 ml of distilled water under slight heating, then the solution thus obtained is poured into the solution being in the tank.

5. Preparation of the composition

The potassium sodium tartrate solution according to 1.b), then the L-(+)-ascorbic acid solution according to 2 are poured under stirring into the solution according to 2 are poured under stirring into the solution being in the tank. The volume of the solution being in the tank is supplemented to 98 l with distilled water. Then the pH of the solution is measured: it must be between 1.9 and 4. If the pH is above 4.0, it is adjusted to about 3.0 by the addition of further amounts of L-ascorbic acid. Finally the volume of the solution is supplemented to 100 liters.

The solution thus obtained is left to stand for 12 to 24 hours. In the meantime the solution clarifies, its color turns to yellowish green. After quality control the solution can be formulated.

100 ml of the thus-obtained solution comprises the following components:

| | | |
|---|---|---|
| ammonium metavanadate | NH$_4$VO$_3$ | 0.028 g |
| sodium fluoride | NaF | 0.020 g |
| glycine | C$_2$H$_5$NO$_2$ | 0.23 g |
| copper(II)-sulfate | CuSO$_4$.5H$_2$O | 0.10 g |
| zinc sulfate | ZnSO$_4$.5H$_2$O | 0.50 g |
| ammonium molybdate | (NH$_4$)$_6$Mo$_7$O$_{24}$.4H$_2$O | 0.035 g |
| nickel(II)-sulfate | NiSO$_4$.7H$_2$O | 0.052 g |
| cobalt(II)-chloride | CoCl$_2$.6H$_2$O | 0.010 g |
| ethylenediaminetetraacetic acid salt (EDTA Na$_2$.2H$_2$O) | C$_{10}$H$_{14}$N$_2$O$_8$Na$_2$.2H$_2$O | 0.30 g |
| L-(+)-ascorbic acid | C$_6$H$_8$O$_6$ | 0.030 g |
| iron(II)-sulfate | FeSO$_4$.7H$_2$O | 1.0 g |
| iron(II)-sulfate | FeSO$_4$.7H$_2$O | 1.0 g |
| magnesium sulfate | MgSO$_4$.7H$_2$O | 0.41 g |
| succinic acid | C$_4$H$_6$O$_4$ | 0.050 g |
| manganese(II)-sulfate | MnSO$_4$.H$_2$O | 0.094 g |
| L-(+)-tartaric acid | C$_4$H$_6$O$_6$ | 0.050 g |
| boric acid | H$_3$BO$_3$ | 0.060 g |
| glycerol (87%) | C$_3$H$_8$O$_3$ | 0.60 g |
| potassium sodium tartrate | C$_4$H$_4$O$_6$KNa.4H$_2$O | 0.20 g |

Example 2

The process of Example 1 is followed except that the amounts of starting materials are chosen in such a manner that 100 ml of the ready-made solution comprise the following amounts of the components:

| | |
|---|---|
| ammonium metavanadate | 0.068 g |
| sodium fluoride | 0.30 g |
| glycine | 1.94 g |
| copper(II)-sulfate | 0.012 g |
| zinc sulfate | 2.85 g |
| ammonium molybdate | 0.020 g |
| nickel(II)-sulfate | 0.070 g |
| cobalt(II)-chloride | 0.0021 g |
| ethylenediaminetetraacetic acid salt (EDTA Na$_2$.2H$_2$O) | 0.20 g |
| L-(+)-ascorbic acid | 0.40 g |
| iron(II)-sulfate | 0.153 g |
| magnesium sulfate | 2.94 g |
| succinic acid | 0.030 g |
| manganese(II)-sulfate | 0.23 g |
| L-(+)-tartaric acid | 1.94 g |
| boric acid | 0.30 g |
| glycerol (87%) | 7.92 g |
| potassium sodium tartrate | 0.10 g |

Example 3

The process of Example 1 is followed except that the amounts of starting materials are chosen in such a manner that 100 ml of the ready-made solution comprise the following amounts of the components:

| | |
|---|---|
| ammonium metavanadate | 0.576 g |
| sodium fluoride | 0.95 g |
| glycine | 0.50 g |
| copper(II)-sulfate | 0.99 g |

| -continued | |
|---|---|
| zinc sulfate | 1.00 g |
| ammonium molybdate | 0.768 g |
| nickel(II)-sulfate | 1.92 g |
| cobalt(II)-chloride | 0.10 g |
| ethylenediaminetetraacetic acid salt (EDTA Na$_2$.2H$_2$O) | 2.97 g |
| L-(+)-ascorbic acid | 1.94 g |
| iron(II)-sulfate | 1.50 g |
| magnesium sulfate | 0.60 g |
| succinic acid | 1.98 g |
| manganese(II)-sulfate | 1.96 g |
| L-(+)-tartaric acid | 0.10 g |
| boric acid | 0.98 g |
| glycerol (87%) | 1.0 g |
| potassium sodium tartrate | 9.78 g |

Example 4

The process of Example 1 is followed except that the amount of starting materials is chosen in such a manner that 100 ml of the ready-made solution comprise the following amounts of the components:

| ammonium metavanadate | 0.0011 g |
|---|---|
| sodium fluoride | 0.012 g |
| glycine | 0.11 g |
| copper(II)-sulfate | 0.50 g |
| zinc sulfate | 0.11 g |
| ammonium molybdate | 0.0011 g |
| nickel(II)-sulfate | 0.012 g |
| cobalt(II)-chloride | 0.97 g |
| ethylenediaminetetraacetic acid salt (EDTA Na$_2$.2H$_2$O) | 0.011 g |
| L-(+)-ascorbic acid | 0.012 g |
| iron(II) sulfate | 5.76 g |
| magnesium sulfate | 0.206 g |
| succinic acid | 0.011 g |
| manganese(II)-sulfate | 0.021 g |
| L-(+)-tartaric acid | 0.011 g |
| boric acid | 0.011 g |
| glycerol (87%) | 0.21 g |
| potassium sodium tartrate | 0.012 g |

The results of tests and examinations carried out for determining the pharmaceutical activity of the composition of the invention are described in detail below.

The tests and examinations were carried out in several institutes under the control of a doctor.

The patients being the subjects of the tests were male and female of different age. They received the composition according to the invention in solution form (1 ml corresponds to about 18 drops). The drops comprising the composition were administered in tea or soft drink. In addition to the drops, the patients were also administered 100 to 300 mg of ascorbic acid per day in the form of tablets or an aqueous solution, depending on the number of drops received. The patients suffering from gastric anacidity were optionally administered acid, too.

A) Test of pain-killer activity in case of chronic pains deriving from degenerative locomotor disorders Method: random, double-blind, with placebo control.

Place of the test: Orthopedic Clinic of the Semmelweis Medical University, Budapest.

The composition of Example 1 was administered to adult patients in the following doses:

the patients having a weight of more than 70 kg received 3×20 drops daily for 1 week, then 2×20 drops for 2 weeks and—depending on the improvement—2×10 or 1×10 drops daily for further 2 weeks, the patients having a weight of less than 70 kg received 2×20 drops daily for 1 week, then 2×20 drops for 2 weeks and—depending on the improvement—1×10 drops daily for further 1 or 2 weeks.

The test covered 156 patients from which 76 patients (Group I) received effective composition, while 80 patients (Group II) were administered placebo. Improvement was observed in Group I with 57 patients (75%) and in Group II with 26 patients (32.5%). In Groups I and II the condition of 19 (25%) and 54 (67.5%) patients, respectively, remained constant.

The test results classified according to the specific disorders of the patients are summarized in Table 1.

TABLE 1

| Diagnosis | Number of patients | | |
|---|---|---|---|
| | total | improved (%) | unchanged (%) |
| Periarthritis humeroscapularis | 5 | 5 (100) | 0 (0) |
| Osteoporosis | 8 | 7 (87.5) | 1 (12.5) |
| Spondylosis dors. et lumb. | 19 | 15 (79) | 4 (21) |
| Arthrosis genus | 12 | 9 (75) | 3 (25) |
| Lumbago, lumboischialgia, stenosis canalis spinalis | 3 | 2 (67) | 1 (33) |
| Other: arthrosis cubiti, arthrosis radiocarp., osteomyelitis, PcP, necr.cap. fem. | 13 | 10 (77) | 3 (23) |

B) Testing of pain-killer activity in case of chronic pain syndromes accompanying tumorous diseases Method: randomized, with morphine control.

The tests were carried out in the State Oncological Clinic, Budapest.

35 patients were involved in the test, from which 17 patients received morphine and 1 drop of the composition of Example 2, calculated for 1 kg of body weight, at each treatment (Group I), while 18 patients were administered only morphine (Group II). In Group I the dose of morphine was reduced to the half of the dose received by the patients of Group II.

Total pain easing could be achieved in the case of 12 patients (71%) in Group I, while the same could be attained by the administration of double morphine doses with 11 (61%) patients in Group II. Reduction but not easing of pain was observed in Groups I and II in case of 5 (29%) and 7 (39%) patients, respectively.

C) Examination of changes of clinical condition of children suffering from mucoviscidosis Mucoviscidosis is a congenital illness based on genetic lesion and is considered as an incurable disease even today. Its most conspicuous manifestation is that the product of the glands becomes highly viscous, contrary to the product of the normal glands. Therefore, the thick discharge produced by the glands adhere to the surface of the lungs and respiratory tracks covered by raucous membrane, it cannot be discharged spontaneously. The accumulated discharge and the pathogens dwelling in it will result in permanent inflammation which can lead to the destruction of the lungs. In the digestive tract the most severe consequence is the insufficient enzyme level in the duodenum due to the condensed pancreatic fluid which results in decreased digestion and utilization of the nutritive substances. As a result, the patients have abundant, undigested stool and still suffer from chronic lack of energy.

The lifetime treatment is focused on the dissolution of the thick discharge and the substitution of the missing enzymes and vitamins. Nevertheless, not all insufficiencies can be solved completely even in spite of the most careful treatment. In addition, the susceptibility to infections is also higher.

The test was started on 40 children suffering from mucoviscidosis, from which 5 children gave up the taking of the composition of the invention. Thus, the results relate to the treatment of only 35 children. The age of the children varied between 3 and 18 years.

Method: the composition according to Example 3 was administered for 6 months in a daily dose of 1 drop per kg body weight.

The test was carried out in the Helm Pál Children's Hospital, Budapest.

As a result of the treatment with the composition of the invention, the general state of health and physical activity of a significant part of the children improved. School-children could better tolerate the school-related loads. The appetite of a great part of the children improved and, as a consequence, their body weight increased.

The change of the iron and zinc content in the blood serum of the patients was measured and it was found that the zinc and iron levels increased in the case of 32 (91%) and 18 (51%) patients, respectively, and played with high probability a significant role in the improvement of the patients. An other favorable result was that also the ferritin content increased in the blood serum of 25 (71%) patients.

The observations relating to the clinical condition of the patients are comprised in Table 2.

TABLE 2

|  | Improved No. of patients | % | Unchanged No. of patients | % |  |  |
|---|---|---|---|---|---|---|
| Body weight | 28 | (80) | 7 | (20) |  |  |
| Height | 30 | (86) | 5 | (14) |  |  |
|  |  |  | A | % | B | % |
| State of health | 27 | (77) | 5 | (14) | 3 | (9) |
| Physical activity | 24 | (69) | 6 | (17) | 5 | (14) |

TABLE 2-continued

|  | Improved No. of patients | % | Unchanged No. of patients | % |  |  |
|---|---|---|---|---|---|---|
| Appetite | 28 | (80) | 4 | (11) | 3 | (9) |
| Stool | 15 | (43) | 10 | (54) | 1 | (3) |

A = the feature was favorable previously, too
B = the feature was unfavorable previously The above test unambiguously prove that the composition according to the invention ensures very favorable clinical results in the treatment of mucoviscidosis and chronic pain syndromes deriving from degenerative locomotor diseases or accompanying diseases of tumorous origin.

The dose of the pharmaceutical composition of the invention depends on the state, body weight and illness of the patient. The daily dose may vary between 5 and 500 drops, and it amounts suitably to 20–150 drops, preferably to 40–80 drops per day.

What we claim is:

1. A method of treating mucoviscidosis or a chronic pain syndrome derived from either a locomotor disease of a degenerative nature or from a disease of tumorous origin, which comprises the step of administering to a patient in need of said treatment, a therapeutically effective amount of a pharmaceutical composition, which consists essentially of:
   i) one or more, pharmaceutically acceptable, water soluble compounds of boron, fluorine, magnesium, vanadium, manganese, iron, cobalt, nickel, copper, zinc and molybdenum, which compounds do not precipitate with each other or with the other components of the composition and exhibit a neutral or acidic pH in an aqueous medium;
   ii) glycine;
   iii) glycerol;
   iv) L-(+)-ascorbic acid;
   v) succinic acid;
   vi) a neutral or acidic and water-soluble, pharmaceutically acceptable salt of ethylenediamine tetraacetic acid;
   vii) potassium sodium tartrate; and
   viii) L-(+)-tartaric acid.

* * * * *